US012564308B2

(12) United States Patent
Kobayashi

(10) Patent No.: US 12,564,308 B2
(45) Date of Patent: Mar. 3, 2026

(54) IMAGE PICKUP UNIT, ENDOSCOPE, AND METHOD FOR MANUFACTURING IMAGE PICKUP UNIT

(71) Applicant: OLYMPUS CORPORATION, Tokyo (JP)

(72) Inventor: Hiroshi Kobayashi, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 389 days.

(21) Appl. No.: 18/125,962

(22) Filed: Mar. 24, 2023

(65) Prior Publication Data

US 2023/0225585 A1      Jul. 20, 2023

Related U.S. Application Data

(63) Continuation of application No. PCT/JP2021/015860, filed on Apr. 19, 2021.

(51) Int. Cl.
*A61B 1/00*          (2006.01)
*A61B 1/05*          (2006.01)

(52) U.S. Cl.
CPC ............ *A61B 1/00064* (2013.01); *A61B 1/05* (2013.01); *A61B 1/00163* (2013.01)

(58) Field of Classification Search
CPC ... A61B 1/00064; A61B 1/05; A61B 1/00163; A61B 1/07; A61B 1/0011; A61B 1/051; A61B 1/00096; G02B 7/00; H04N 25/70; H10F 39/12
See application file for complete search history.

(56) References Cited

U.S. PATENT DOCUMENTS

| | | | |
|---|---|---|---|
| 2004/0189855 A1 | 9/2004 | Takasaki et al. | |
| 2006/0038204 A1 | 2/2006 | Takasaki et al. | |
| 2008/0231739 A1 | 9/2008 | Takasaki et al. | |
| 2019/0082944 A1 | 3/2019 | Fujimori | |
| 2021/0255451 A1* | 8/2021 | Maeda ..................... G02B 7/02 |

FOREIGN PATENT DOCUMENTS

| | | | | |
|---|---|---|---|---|
| EP | 1 463 120 A2 | 9/2004 | | |
| JP | 2004-296740 A | 10/2004 | | |
| JP | 2004312666 A | * 11/2004 | ............. H10F 39/12 |
| JP | 2011-128355 A | 6/2011 | | |
| JP | 2012-018993 A | 1/2012 | | |
| JP | 2012-203195 A | 10/2012 | | |
| WO | 2017/203594 A1 | 11/2017 | | |
| WO | 2020/084728 A1 | 4/2020 | | |

OTHER PUBLICATIONS

International Search Report dated Jul. 20, 2021 received in PCT/JP2021/015860.

* cited by examiner

*Primary Examiner* — Michael J Carey
*Assistant Examiner* — Christen A. Sharpless
(74) *Attorney, Agent, or Firm* — Scully, Scott, Murphy & Presser, P.C.

(57)          ABSTRACT
An image pickup unit includes a first optical device including a lens and a spacer arranged around the lens and having a circular inner circumference, the spacer having a thickness continuously decreasing outward, an adhesive layer disposed on an adhesive surface of the spacer of the first optical device, a second optical device adhered to the first optical device by the adhesive layer, and an imager receiving light condensed by an optical system including the first optical device and the second optical device.

7 Claims, 9 Drawing Sheets

IMAGE PICKUP UNIT, ENDOSCOPE, AND METHOD FOR MANUFACTURING IMAGE PICKUP UNIT

CROSS REFERENCE TO RELATED APPLICATION

This application is a continuation application of PCT/JP2021/015860 filed on Apr. 19, 2021, the entire contents of which are incorporated herein by this reference.

BACKGROUND OF THE INVENTION

1. Field of the Invention

The present invention relates to an image pickup unit in which a plurality of optical devices is adhered using an adhesive, an endoscope including the image pickup unit, and a method for manufacturing the image pickup unit.

2. Description of the Related Art

It is important to reduce a size of an image pickup unit of an endoscope for reducing invasion. As a method for efficiently manufacturing a small-sized image pickup unit, there is a wafer level manufacturing method of cutting a stacked wafer in which a plurality of device wafers each including a plurality of optical devices is stacked.

Japanese Unexamined Patent Application Publication No. 2012-18993 discloses an image pickup unit constituted of a wafer level stacked body. The image pickup unit is fabricated by bonding an optics wafer including a plurality of optical devices and a stacked wafer including a plurality of image pickup devices, and then singulating the bonded wafer by cutting. The stacked wafer includes spacers that define a gap between the stacked optical devices.

Japanese Unexamined Patent Application Publication No. 2011-128355 discloses a manufacturing method in which a portion of a notch is formed in an outer peripheral portion of a spacer of a wafer level stacked body and by injecting an adhesive into the portion of the notch, adhering the outer peripheral portion of the spacer in a state abutting against another substrate.

SUMMARY OF THE INVENTION

An image pickup unit according to an embodiment of the present invention includes: a first optical device including a lens and a spacer arranged around the lens and having a circular inner circumference, the spacer having a thickness continuously decreasing outward; an adhesive layer disposed on an adhesive surface of the spacer of the first optical device; a second optical device adhered to the first optical device by the adhesive layer; and an imager receiving light condensed by an optical system including the first optical device and the second optical device.

An endoscope according to an embodiment of the present invention including an image pickup unit at a distal end portion of an insertion portion, the image pickup unit includes: a first optical device including a lens and a spacer arranged around the lens and having a circular inner circumference, the spacer having a thickness continuously decreasing outward; an adhesive layer disposed on an adhesive surface of the spacer of the first optical device; a second optical device adhered to the first optical device by the adhesive layer; and an imager receiving light condensed by an optical system including the first optical device and the second optical device.

A method for manufacturing an image pickup unit according to an embodiment of the present invention includes: fabricating a first wafer including a first optical device including a lens and a spacer arranged around the lens and having a circular inner circumference, the spacer having a thickness continuously decreasing outward, and a second wafer including a second optical device; disposing an adhesive layer made of an uncured adhesive on a flat plate; transferring the adhesive to an adhesive surface by abutting the adhesive surface of the spacer of the first wafer against the adhesive layer on the flat plate and then separating the adhesive surface from the adhesive layer; adhering the second wafer and the first wafer using the adhesive, adhering an imager receiving light condensed by an optical system including the first optical device and the second optical device; and cutting a stacked wafer including the first wafer, the second wafer, and the imager into singulated image pickup units each including the first optical device, the second optical device, and the imager.

DETAILED DESCRIPTION OF THE PREFERRED EMBODIMENT(S)

First Embodiment

Figure 1:
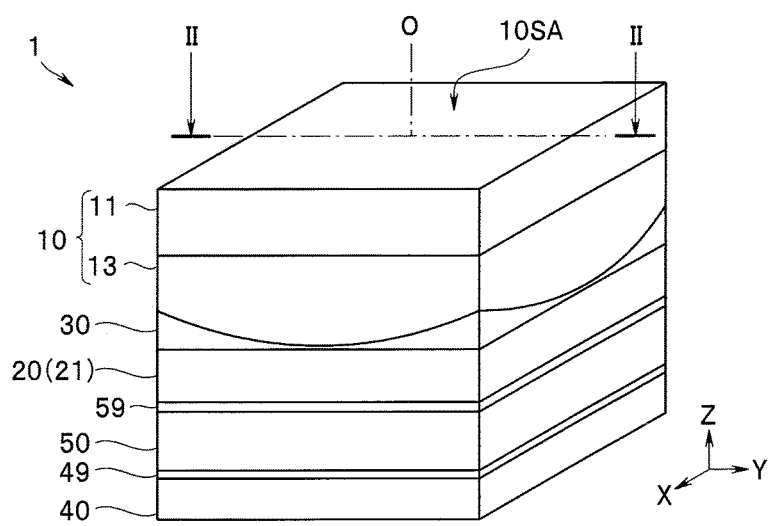
FIG. 1 is a perspective view of an image pickup unit according to a first embodiment.
Figure 2:
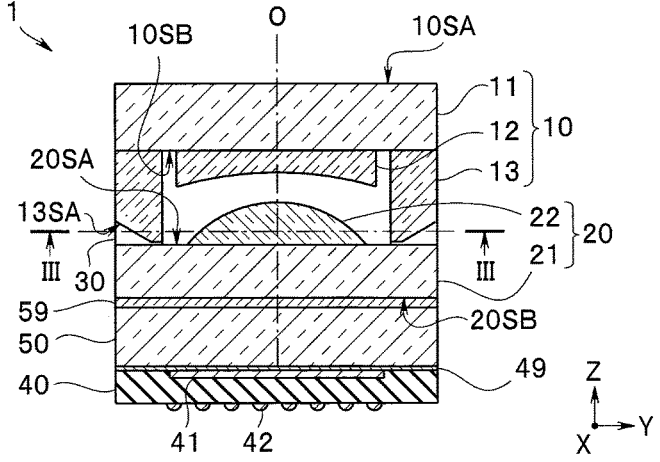
FIG. 2 is a cross-sectional view taken along a line II-II of FIG. 1.
Figure 3:
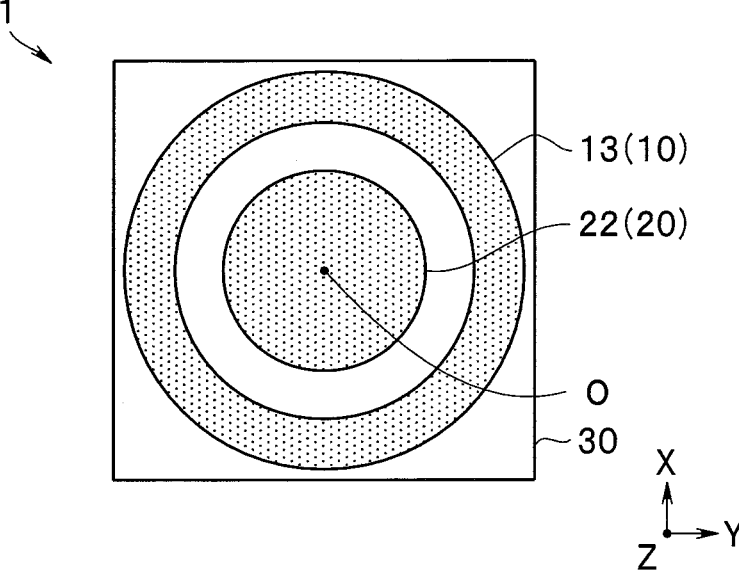
FIG. 3 is a cross-sectional view taken along a line of FIG. 2.

As illustrated in FIGS. 1, 2, and 3, in an image pickup unit 1 of the present embodiment, a first optical device 10, a second optical device 20, a third optical device 50, and an image pickup device 40 which is an imager are stacked in the order described above. The first optical device 10 and the second optical device 20 are adhered to each other by an adhesive layer 30. The second optical device 20 and the third optical device 50 are adhered to each other by an adhesive layer 59. The third optical device 50 and the image pickup device 40 are adhered to each other by an adhesive layer 49.

In the following description, the accompanying drawings based on each embodiment are schematic. The relationship between a thickness and a width of each portion, a ratio of the thickness of each portion, and the like are different from the actual configuration. The accompanying drawings also include portions having mutually different dimensional relationships and ratios. In addition, there may be a case that illustration of some of constituent elements and assignment of signs are omitted.

The first optical device 10 has a glass plate 11 as a base substrate, which is a first transparent substrate. The first transparent substrate includes a first principal surface 10SA, which is a light incident surface, and a second principal surface 10SB on the opposite side of the first principal surface 10SA. The first optical device 10 is a hybrid lens device in which a lens 12 made of a resin and a spacer 13 made of a resin are disposed on the second principal surface 10SB. The spacer 13 having a ring shape is arranged around the lens 12.

The second optical device 20 has a glass plate 21 as a base substrate in which a third principal surface 20SA and a fourth principal surface 20SB on the opposite side of the third principal surface 20SA are included. The second optical device 20 is a hybrid lens device in which a lens 22 made of a resin is disposed on the third principal surface 20SA. The third optical device 50 is a cover glass for protecting the image pickup device or an infrared cut filter device made of glass having a function of blocking infrared rays. The image pickup device 40 includes a light receiving portion 41 and an external electrode 42.

A subject image condensed by an optical system including the first optical device 10, the second optical device 20, and the third optical device 50 is converted into an electric signal by the light receiving portion 41 of the image pickup device 40, and the electric signal is outputted from the external electrode 42.

As illustrated in FIG. 2, a thickness (a dimension in a direction parallel to an optical axis O) of the spacer 13 having a circular inner circumference and a circular outer periphery continuously decreases outward. As will be described later, the adhesive layer 30 is disposed on the spacer 13 using a transfer method, but no air bubbles remain on an adhesive surface 13SA of the spacer 13. Since the adhesive strength of the adhesive layer 30 between the first optical device 10 and the second optical device 20 is high, the image pickup unit 1 has high reliability.

The lens 12, the spacer 13, and the lens 22 are, for example, an acrylic based resin or an epoxy resin. The glass plates 11 and 21, which are transparent substrates, are made of borosilicate glass, quartz glass, or sapphire glass, for example. The transparent substrate may be a transparent resin plate. The adhesive layers 30, 59 and 49 are, for example, a transparent resin of an ultraviolet curable type, a thermosetting type, or an ultraviolet heat combined curable type.

As will be described later, a configuration of the optical system, that is, the type, the number, and the stacking order of the optical devices can be variously modified in accordance with the specification. For example, a patterned light shielding film having an aperture function may be disposed on the principal surface of the optical device.

<Manufacturing Method for Image Pickup Unit>

Figure 4:
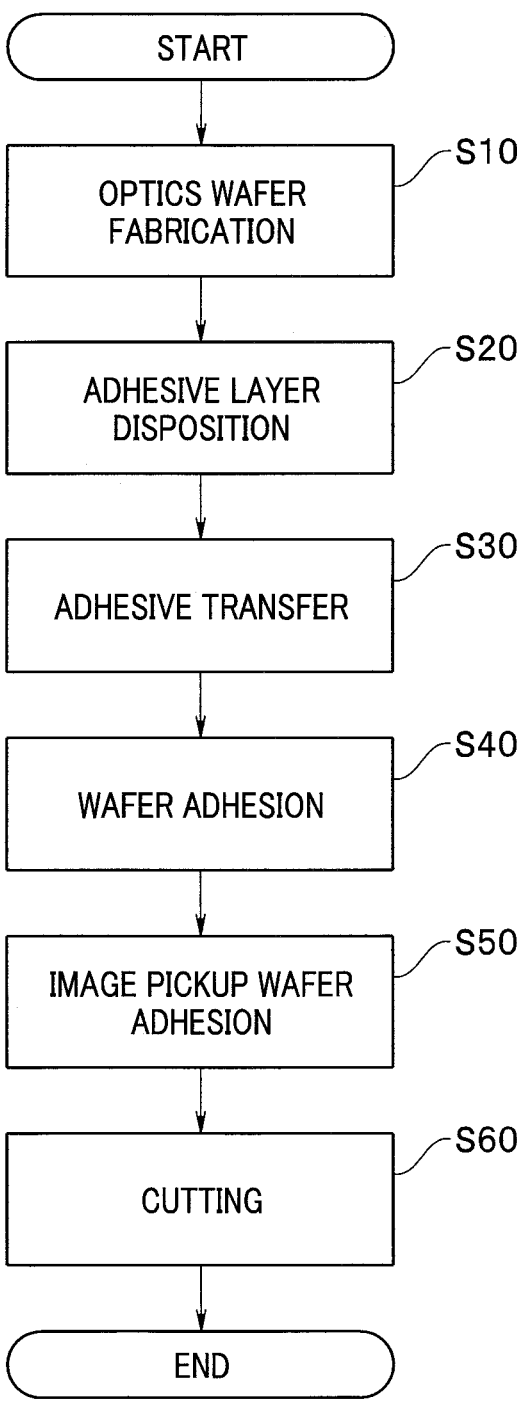
FIG. 4 is a flowchart of a method for manufacturing the image pickup unit according to the first embodiment.

A method for manufacturing the image pickup unit 1 will be described with reference to a flowchart of FIG. 4.

<Step S10> Optics Wafer Fabrication

Figure 5A:
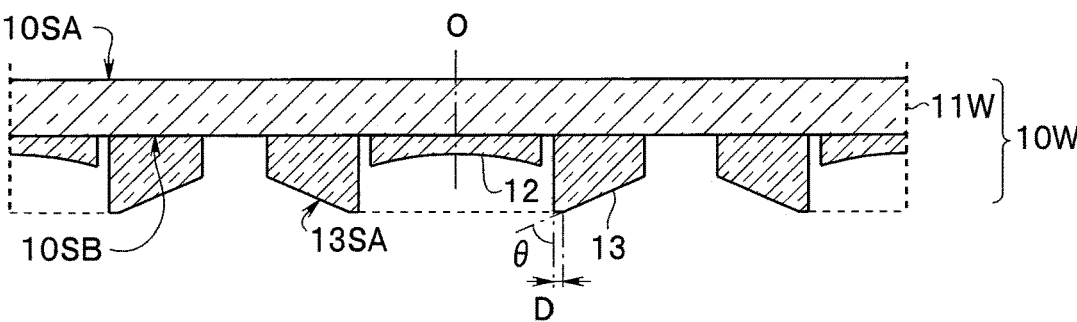
FIG. 5A is a cross-sectional view for explaining the method for manufacturing the image pickup unit according to the first embodiment.

As illustrated in FIG. 5A, a plurality of lenses 12 and a plurality of spacers 13 having a ring shape and surrounding the respective lenses 12 are arranged on the second principal surface 10SB of a glass wafer 11W, and a first optics wafer 10W is fabricated.

On the second principal surface 10SB, a plurality of optical functional portions each including the lens 12 and the spacer 13 is two dimensionally arranged in a lattice pattern.

A thickness of the glass wafer 11W is determined in accordance with the specification of the image pickup unit 1, but is preferably equal to or more than 50 μm and equal to or less than 1 mm, for example, for miniaturization. Note that when the glass wafer 11W is cut, the cut glass wafer 11W becomes the glass plate 11 of the first optical device 10.

For example, the lens 12 and the spacer 13 are fabricated by a mold forming method in which an uncured resin is disposed on the glass wafer 11W, and the resin is cured by irradiation with ultraviolet rays in a state where a mold having a concave portion with a predetermined inner surface shape is pressed against the glass wafer 11W. Since the inner surface shape of the mold is transferred to the lens 12 as an outer surface shape thereof, an aspherical lens and the spacer 13 having a complicated shape can be easily fabricated by the mold forming method. Note that the lens 12 and the spacer 13 may be fabricated by an inkjet method, or the like.

The spacer 13 having a ring shape has the thickness (a dimension in a direction parallel to the optical axis O) linearly decreasing outward when the optical axis O of each lens 12 is the center. In other words, a bottom surface which is the adhesive surface 13SA of the spacer 13 includes a tapered surface inclined from an optical axis side toward the circumference. A thickness of the spacer 13 may decrease outward in a curved manner An inclination angle θ (see FIG. 5A) which is an angle formed by an inner circumferential surface of the spacer 13 and the adhesive surface 13SA is, for example, 45 degrees. An inner circumferential region of the adhesive surface 13SA has a constant thickness. For example, a region of the inner circumference of the spacer 13 having a width D (a dimension in a direction orthogonal to the optical axis O) is a parallel surface 13SA2 (see FIG. 7) parallel to the second principal surface 10SB. The width D is, for example, 100 μm.

Figure 5B:
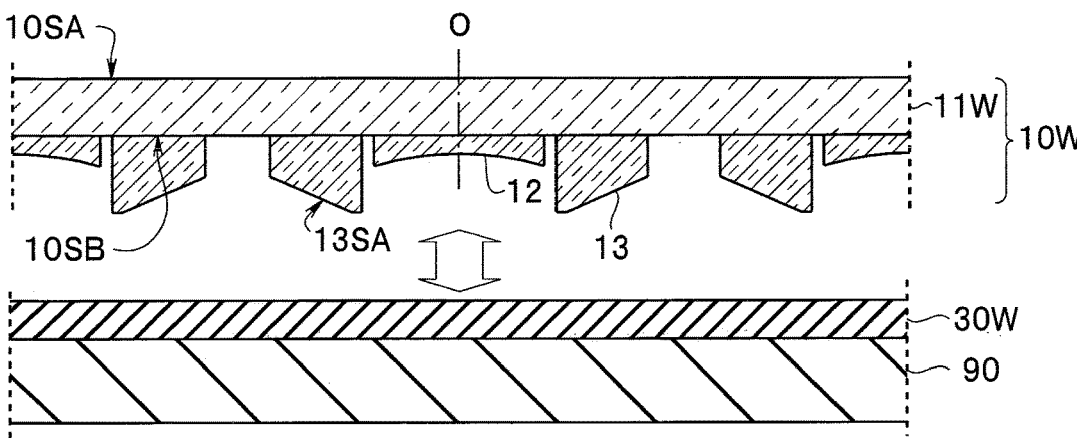
FIG. 5B is a cross-sectional view for explaining the method for manufacturing the image pickup unit according to the first embodiment.
Figure 5C:
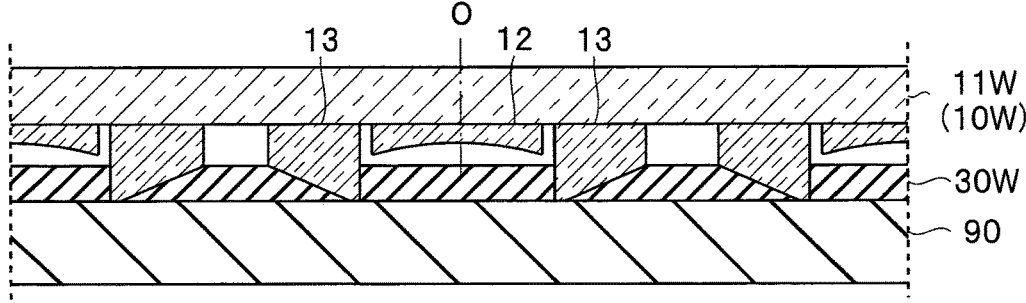
FIG. 5C is a cross-sectional view for explaining the method for manufacturing the image pickup unit according to the first embodiment.
Figure 5D:
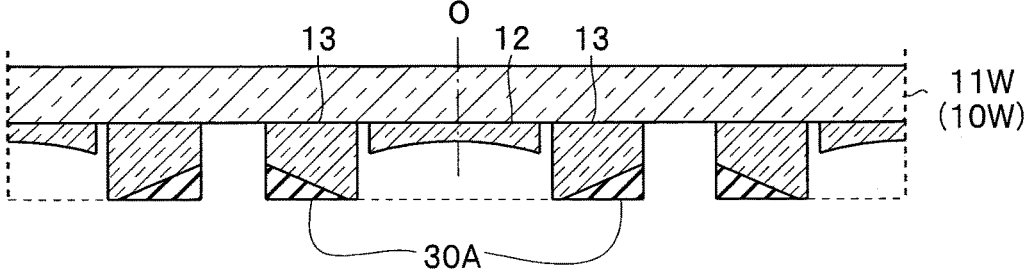
FIG. 5D is a cross-sectional view for explaining the method for manufacturing the image pickup unit according to the first embodiment.
Figure 5E:
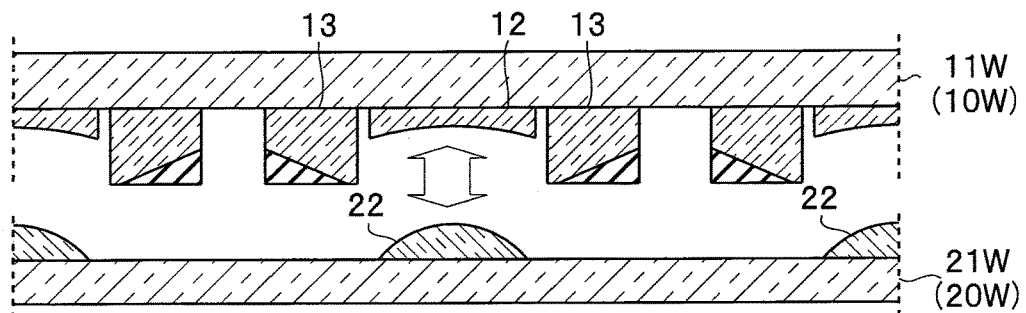
FIG. 5E is a cross-sectional view for explaining the method for manufacturing the image pickup unit according to the first embodiment.

Similarly, a plurality of lenses 22 is arranged on a glass wafer 21W, and a second optics wafer 20W is fabricated (see FIG. 5E). When the glass wafer 21W is cut, the cut glass wafer 21W becomes the glass plate 21 of the second optical device 20. The lens 12 is an aspherical concave lens, and the lens 22 is an aspherical convex lens.

<Step S20> Adhesive Layer Disposition

As illustrated in FIG. 5B, an adhesive layer 30W made of an uncured adhesive is disposed on a flat plate 90.

<Step S30> Adhesive Transfer

As illustrated in FIG. 5C, the adhesive surface 13SA of the spacer 13 of the first optics wafer 10W is abutted against the adhesive layer 30W and then separated, whereby an adhesive 30A is transferred only to the spacer 13 as illustrated in FIG. 5D.

By using the transfer method, it is possible to collectively dispose the adhesive 30A only on each of the adhesive surfaces 13SA of the plurality of spacers 13 of the first optics wafer 10W. Note that when the wafer is cut, the adhesive 30A becomes the adhesive layer 30.

Figure 6:
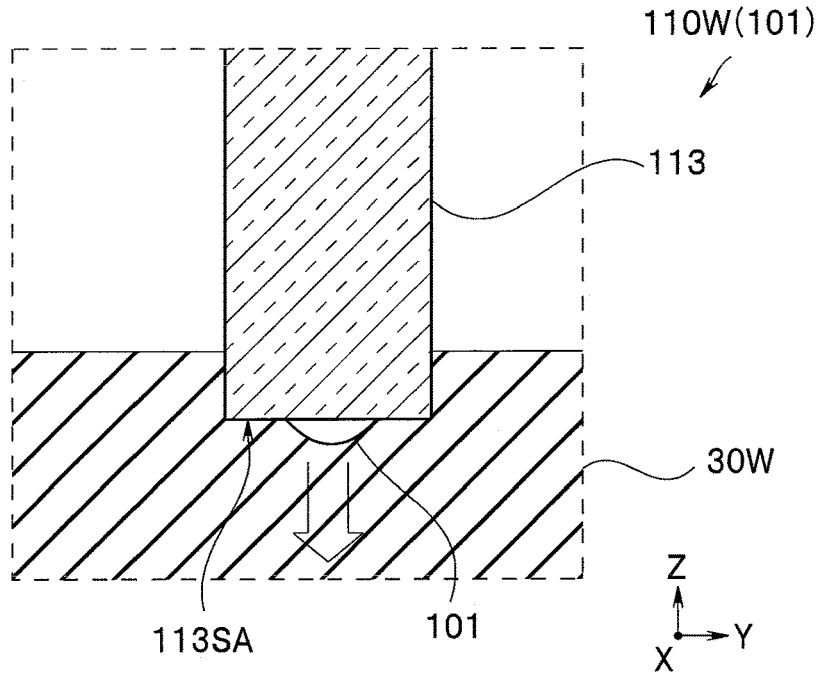
FIG. 6 is a partial cross-sectional view for explaining a method for manufacturing a conventional image pickup unit.

As illustrated in FIG. 6, in a conventional optics wafer 110W in which an adhesive surface 113SA of a spacer 113 is not inclined, when the adhesive surface 113SA enters the adhesive layer 30W, since an area of the adhesive surface 113SA which first comes into contact with the adhesive layer 30W is large, an air bubble 101 may adhere to the adhesive surface 113SA.

Figure 7:
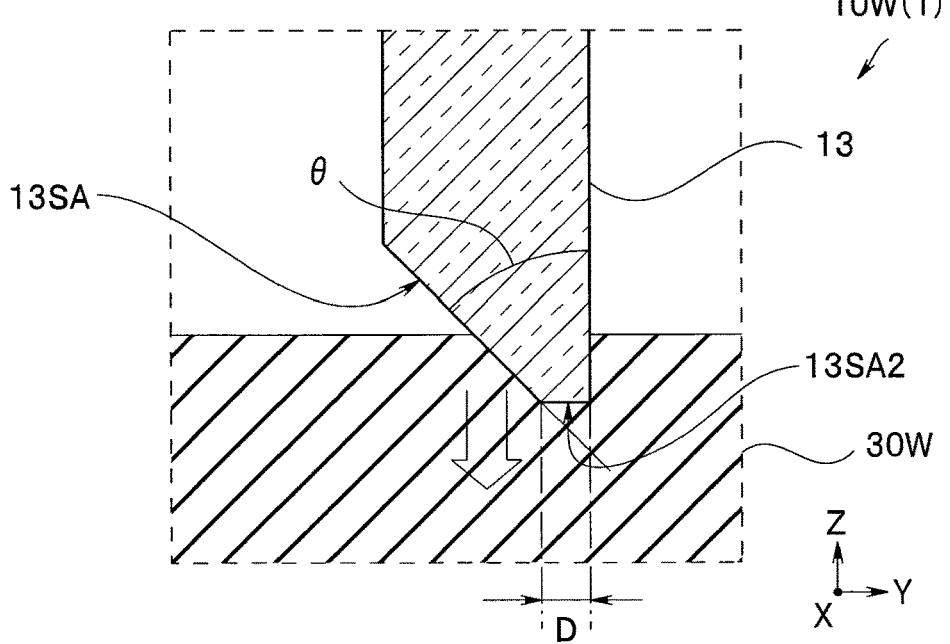
FIG. 7 is a partial cross-sectional view for explaining the method for manufacturing the image pickup unit according to the first embodiment.

On the other hand, as illustrated in FIG. 7, in the first optics wafer 10W in which the adhesive surface 13SA is inclined, since an area of the parallel surface 13SA2 which first comes into contact with the adhesive layer 30W is small, an air bubble does not adhere to the adhesive surface 13SA and the parallel surface 13SA2. In order to prevent adhesion of an air bubble, the inclination angle θ is preferably more than 20 degrees and less than 70 degrees, and particularly preferably more than 30 degrees and less than 60 degrees. In order to prevent adhesion of an air bubble, the width D of the parallel surface 13SA2 of the spacer 13 is preferably less than 300μm, and particularly preferably less than 200 μm.

<Step S40> Wafer Adhesion

Figure 5F:
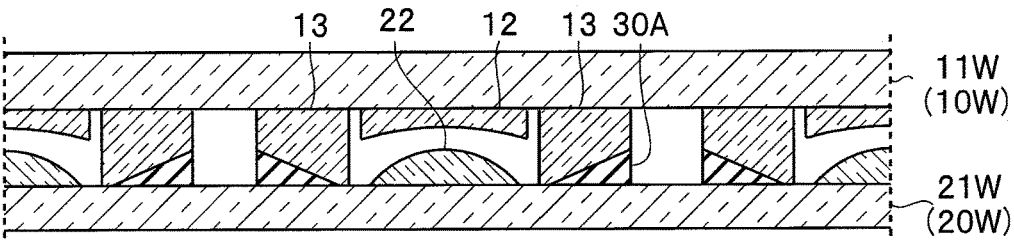
FIG. 5F is a cross-sectional view for explaining the method for manufacturing the image pickup unit according to the first embodiment.

As illustrated in FIGS. 5E and 5F, the first optics wafer 10W and the second optics wafer 20W are adhered using the adhesive 30A.

Since the spacer 13 has the parallel surface 13SA2 having a constant thickness and parallel to the second principal surface 10SB of the first optics wafer 10W at the inner circumference, the spacer 13 and the second optics wafer 20W are in surface contact with the adhesive 30A interposed therebetween, so that a gap between the first optics wafer 10W and the second optics wafer 20W can be particularly stably defined. In order to stably define the gap, the width D of the parallel surface 13SA2 is preferably more than 10 μm, particularly preferably more than 50 μm.

Figure 5G:
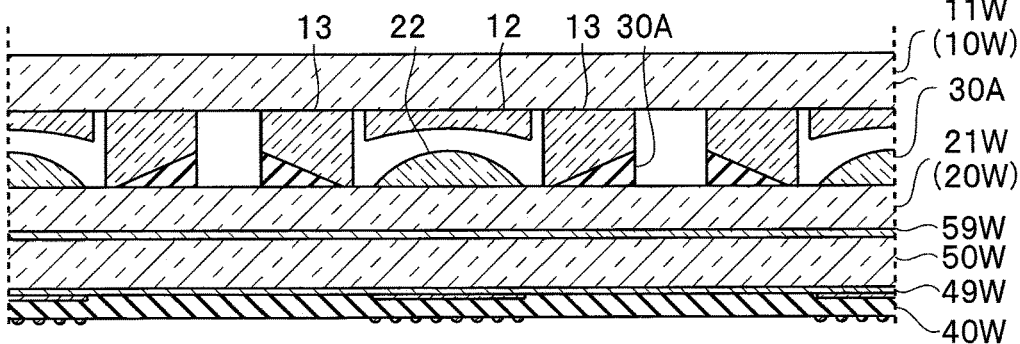
FIG. 5G is a cross-sectional view for explaining the method for manufacturing the image pickup unit according to the first embodiment.

As illustrated in FIG. 5G, a third optics wafer 50W to be the third optical device 50 is adhered to the second optics wafer 20W by the adhesive layer 59W and a stacked optics wafer is fabricated. The adhesive 30A and the adhesive layer 59W are subjected to a curing process by, for example, ultraviolet irradiation, heat treatment, or ultraviolet irradiation and heat treatment.

<Step S50> Image Pickup Wafer Adhesion

As illustrated in FIG. 5G, an image pickup wafer 40W including a plurality of image pickup devices 40 is aligned with the optical axes of the respective lenses 12, 22 and adhered to the third optics wafer 50W of the stacked optics wafer using an adhesive layer 49W. That is, the image pickup wafer 40W receiving light condensed by the optical system including the first optical device 10 and the second optical device 20 is adhered to the stacked optics wafer.

In the method for manufacturing the image pickup wafer 40W, the light receiving portion 41 such as a CMOS light receiving device is formed on a semiconductor wafer by a known semiconductor manufacturing method.

Subsequently, through wirings (not illustrated) are disposed and the image pickup wafer 40W in which the light receiving portion 41 and the external electrode 42 are connected is fabricated.

<Step S60> Cutting

Figure 5H:
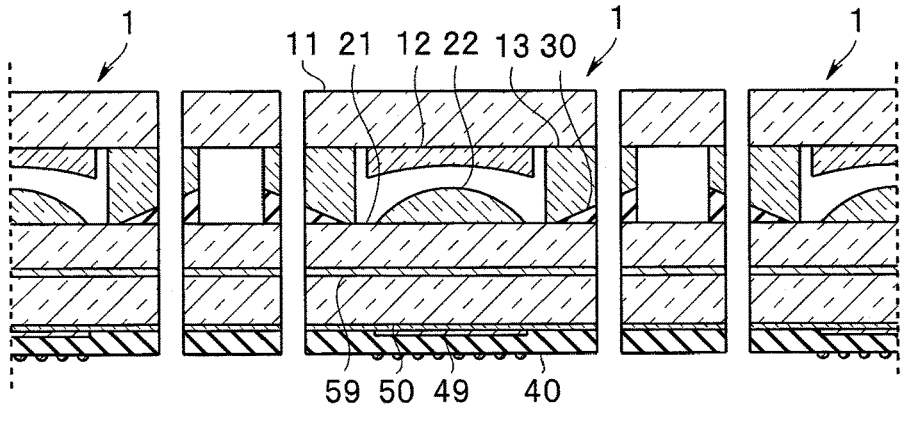
FIG. 5H is a cross-sectional view for explaining the method for manufacturing the image pickup unit according to the first embodiment.
Figure 5H:
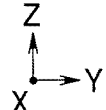

As illustrated in FIG. 5H, the stacked wafer in which the first optics wafer 10W, the second optics wafer 20W, the third optics wafer 50W, and the image pickup wafer 40W are stacked is cut by a blade dicing method, whereby a plurality of image pickup units 1 is fabricated.

The first optical device 10, the second optical device 20, and the third optical device 50 configuring the optical system have the same outer shape and the same outer dimension in a cross section orthogonal to the optical axis O. Since the plurality of optical devices is all rectangular parallelepipeds and has the same shape and the same dimension in the cross section in the direction orthogonal to the optical axis, the optical system is a quadrangular prism.

The cutting step may be, for example, a cutting step by laser dicing or a step of forming a cutting groove by sandblasting or etching.

In the manufacturing method of the present embodiment, the adhesive 30A can be collectively disposed on the spacers 13 of the plurality of first optical devices 10 by using the transfer method, and thus the manufacturing is easy. In addition, since the adhesive surface 13SA is an inclined surface, an air bubble is not generated in the adhesive surface 13SA, and thus the image pickup unit 1 has high reliability.

Modified Example of First Embodiment

Since image pickup units 1A to 1E according to modified examples of the first embodiment are similar to the image pickup unit 1, constituent elements having the same functions are denoted by the same reference numerals and description thereof will be omitted.

First Modified Example of First Embodiment

Figure 8:
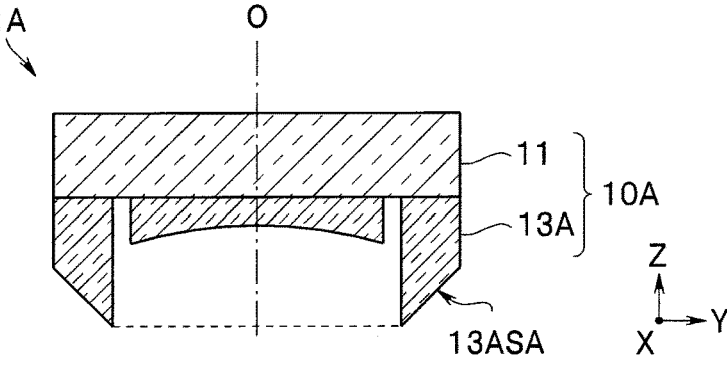
FIG. 8 is a cross-sectional view of an optical device of an image pickup unit according to a first modified example of the first embodiment.

As illustrated in FIG. 8, in a first optical device 10A of an image pickup unit 1A of the present modified example, an entire adhesive surface 13ASA of a spacer 13A is an inclined surface. That is, the adhesive surface 13ASA does not have a parallel surface parallel to the second principal surface 10SB of the first optics wafer 10W in the inner circumference.

In the image pickup unit 1A, when the adhesive is transferred to the spacer 13A, the adhesive surface 13ASA is first used as an adhesive layer. Therefore, an air bubble does not adhere to the adhesive surface 13ASA. In addition, due to line contact between the spacer 13A and the second optics wafer 20W, the gap between the first optics wafer 10W and the second optics wafer 20W can be defined particularly precisely. The spacer 13A after cutting is in line contact with the second optical device 20.

Second Modified Example of First Embodiment

Figure 9:
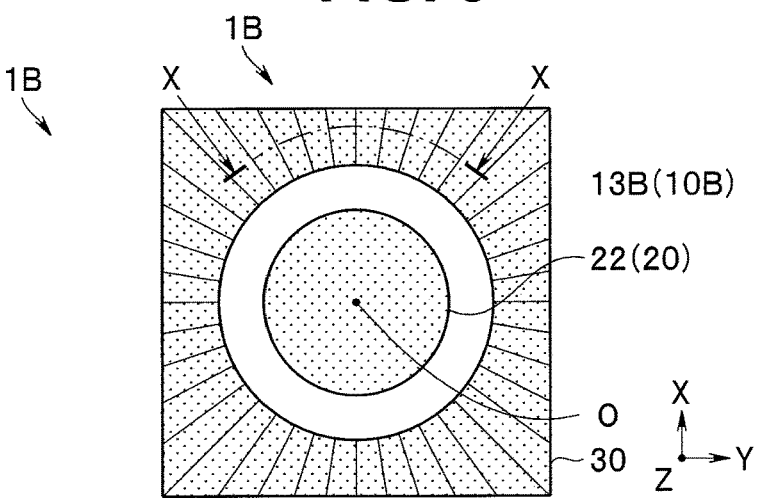
FIG. 9 is a bottom view of an optical device of an image pickup unit according to a second modified example of the first embodiment.
Figure 10:
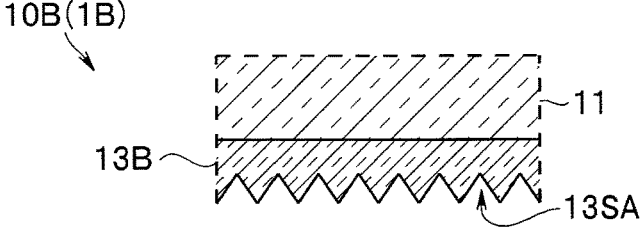
FIG. 10 is a cross-sectional view of an adhesive surface of a spacer taken along a line X-X of FIG. 9.

As illustrated in FIGS. 9 and 10, in an image pickup unit 1B of the present modified example, a thickness of a spacer 13B whose outer periphery is rectangular is changed linearly and repeatedly by increasing and decreasing in a circumferential direction centered on the optical axis O. FIG. 10 is a cross-sectional view taken along an arc centered on an optical axis O of a first optical device 10B, as indicated by a line X-X in FIG. 9. The adhesive surface 13SA of the spacer 13B has a plurality of grooves (trenches) each having a V shape cross section radially centered on the optical axis O, and has a shape in which unevenness is continuous in the circumferential direction. Note that the spacers 13 and 13A may also have a rectangular outer periphery.

When the uncured liquid adhesive 30A is transferred to the spacer 13B, the spacer 13B having the grooves on the adhesive surface 13SA fills the inside of the adhesive 30A by interfacial tension. Therefore, in the image pickup unit 1B, it is easy to dispose the adhesive 30A by the transfer method, and an air bubble is even more unlikely to be generated.

Third Modified Example of First Embodiment

Figure 11:
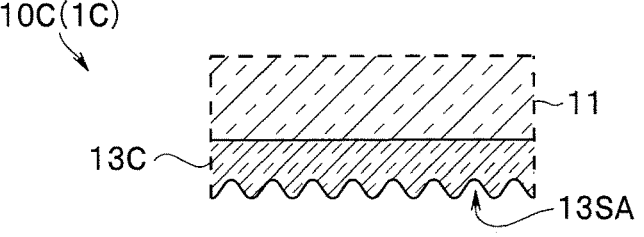
FIG. 11 is a cross-sectional view of the adhesive surface of the spacer of the optical device of the image pickup unit according to a third modified example of the first embodiment.

FIG. 11 is, similar to FIG. 10, a cross-sectional view of an arc centered on an optical axis O of a first optical device 10C of an image pickup unit 1C according to the present modified example. A thickness of a spacer 13C of the image pickup unit 1C of the present modified example illustrated in FIG. 11 is changed repeatedly by increasing and decreasing in a curved manner in the circumferential direction centered on the optical axis O. That is, on the adhesive surface 13SA, there is a plurality of grooves whose cross sections are configured by curves radially centered on the optical axis O.

The image pickup unit 1C has the same effect as that of the image pickup unit 1B.

In a case where the widths and the depths of the grooves of the spacers 13B and 13C are, for example, more than 5 μm and less than 200 μm, the effect is remarkable.

Fourth Modified Example of First Embodiment

Figure 12:
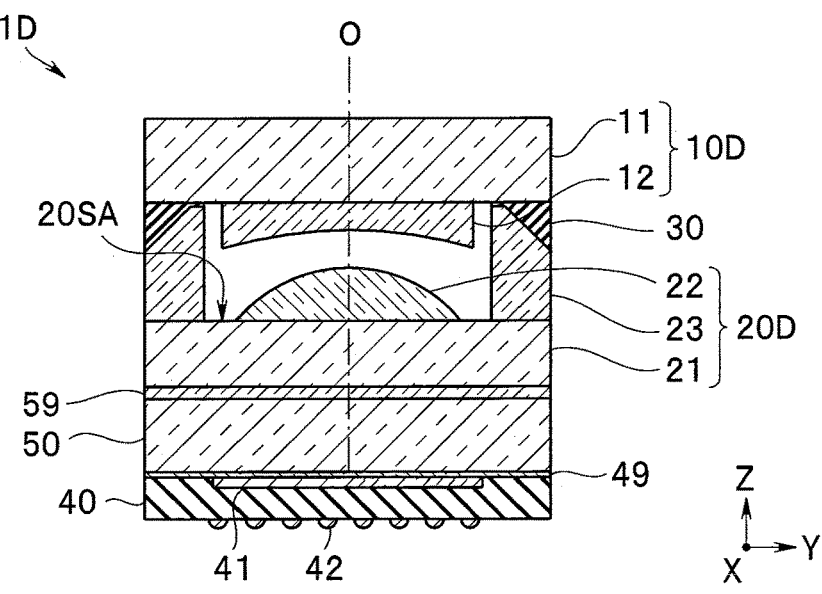
FIG. 12 is a cross-sectional view of an image pickup unit according to a fourth modified example of the first embodiment.

In an image pickup unit 1D of the present modified example illustrated in FIG. 12, the lens 22 and a spacer 23 are disposed on the third principal surface 20SA of the glass plate 21 of a second optical device 20D.

The configuration of the spacer 23 is the same as that of the spacer 13 of the image pickup unit 1 described above. The adhesive surface of the spacer 23 is adhered to the glass plate 11 of a first optical device 10D by the adhesive layer 30.

The image pickup unit 1D has the same effect as that of the image pickup unit 1.

Fifth Modified Example of First Embodiment

Figure 13:
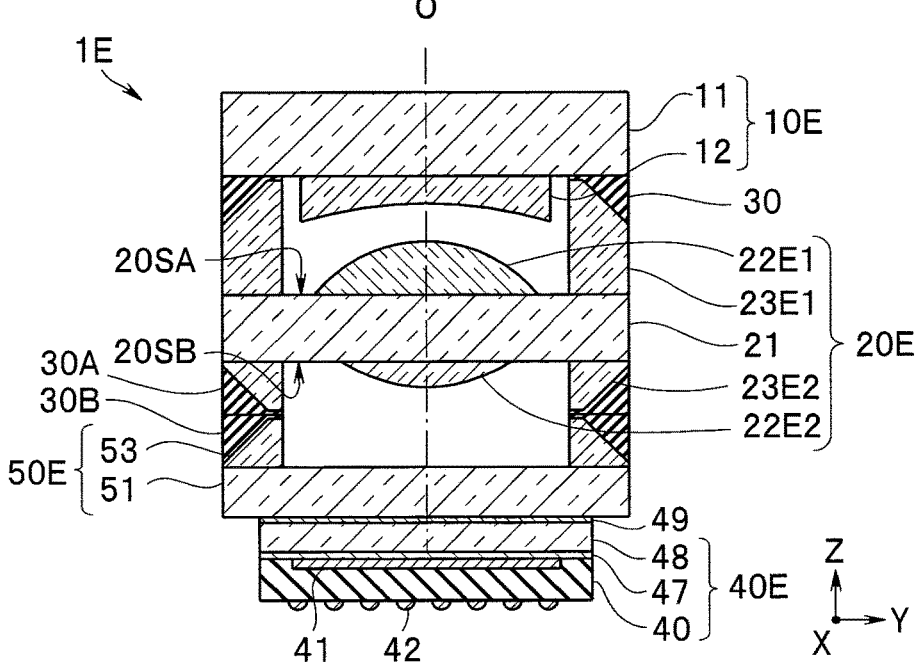
FIG. 13 is a cross-sectional view of an image pickup unit according to a fifth modified example of the first embodiment.

An image pickup unit 1E illustrated in FIG. 13 includes a first optical device 10E, a second optical device 20E, a third optical device 50E, and an imager 40E.

The first optical device 10E is the same as the first optical device 10D. In the second optical device 20E, a lens 22E1 and a spacer 23E1 are disposed on the third principal surface 20SA of the glass plate 21, and a lens 22E2 and a spacer 23E2 are disposed on the fourth principal surface 20SB. A spacer 53 is disposed on the third optical device 50E.

As the spacer 13, thicknesses of the spacers 23E1, 23E2 and 53 decrease continuously outward.

Parallel surfaces of the spacer 23E2 and the spacer 53 face each other and are adhered by the adhesive 30A and an adhesive 30B. As long as one of the thicknesses of the spacer 23E2 and the spacer 53 continuously decreases outward, the other may not change in the thickness.

The imager 40E includes the image pickup device 40, a cover glass 48, and an adhesive layer 47 that adheres the image pickup device 40 and the cover glass 48. In the image pickup unit 1E, the image pickup wafer 40W including the plurality of image pickup devices 40 is singulated into the imagers 40E, and then each of the imagers 40E is adhered to the stacked optics wafer. Alternatively, after the stacked optics wafer is singulated into optical units, the imager 40E may be adhered to each of the optical units.

The image pickup unit 1E has the same effect as that of the image pickup unit 1.

As described above, the configuration of the image pickup unit according to the embodiment can be variously modified in accordance with the specification. That is, the image pickup unit of the embodiment is only required to include: a first optical device including a lens and a spacer arranged around the lens, the spacer having a thickness continuously decreasing outward; an adhesive layer disposed on an adhesive surface of the spacer of the first optical device; a second optical device adhered to the first optical device by the adhesive layer; and an imager receiving light condensed by an optical system including the first optical device and the second optical device.

Although not illustrated, in the image pickup unit of the embodiment, an imager and an optical device may be adhered by an adhesive in a state in which a gap between the imager and the optical device is defined by a spacer having an inclined adhesive surface. In the image pickup unit of the embodiment, three or more optical devices each having a spacer may be stacked.

Second Embodiment

Figure 14:
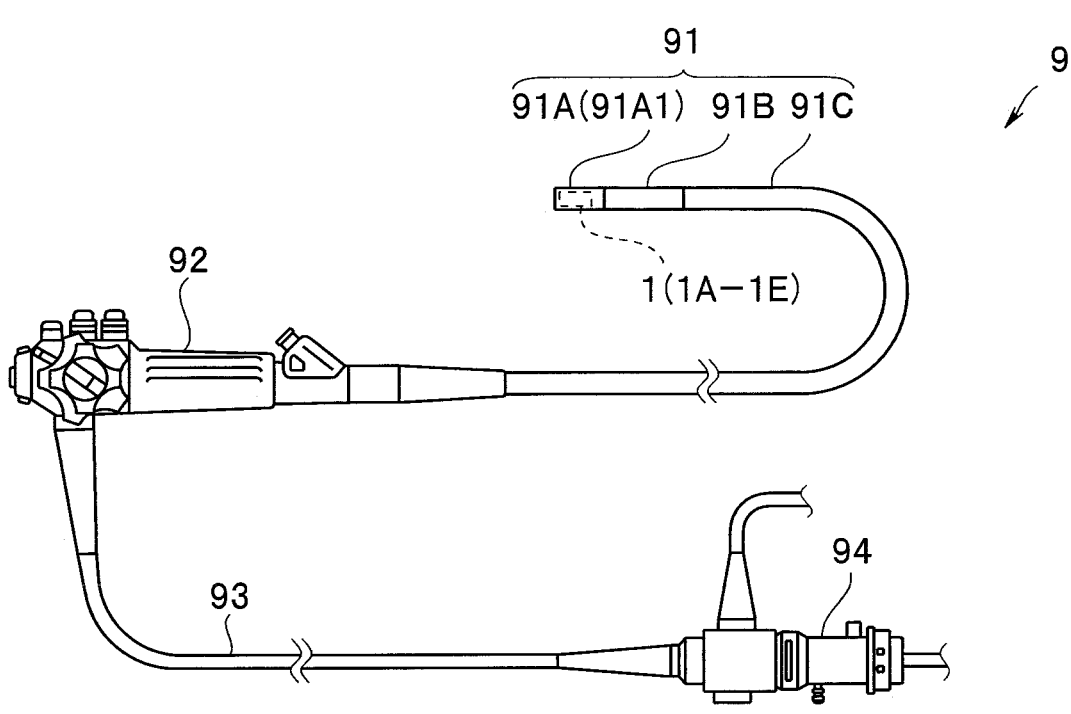
FIG. 14 is a configuration diagram of an endoscope according to a second embodiment.

An endoscope 9 according to the present embodiment illustrated in FIG. 14 includes an insertion portion 91, an operation portion 92, a universal cord 93, and a connector 94.

The insertion portion 91 having an elongated tubular shape is inserted into a body cavity of a living body. In the insertion portion 91, a distal end portion 91A, a bending portion 91B, and a flexible tube 91C are consecutively connected in this order from a distal end side, and the insertion portion 91 has flexibility as a whole. The distal end portion 91A has a rigid member 91A1 in which an image pickup unit 1 is disposed inside. The bending portion 91B is bent in up-down/right-left directions in accordance with a rotation operation of a bending knob of the operation portion 92 for performing a bending operation.

The flexible tube 91C is a tubular member having flexibility that is passively flexible. A treatment instrument insertion channel, a signal line, a fiber bundle, and the like are inserted into the inside of the flexible tube 91C. The signal line extends from the image pickup unit incorporated in the distal end portion 91A to the universal cord 93 via the operation portion 92. The fiber bundle guides light from a light source device, which is an external device, to a distal end surface of the distal end portion 91A.

The operation portion 92 is consecutively connected to a proximal end portion of the insertion portion 91 and includes a plurality of operation members, and the like. The universal cord 93 extends from the operation portion 92. The connector 94 is a connection member to connect the universal cord 93 and the external device.

The endoscope 9 includes the image pickup unit 1 disposed in the rigid member 91A1. As described above, since the image pickup unit 1 has high reliability, the endoscope 9 has high reliability.

It goes without saying that the endoscope 9 including the image pickup units 1A to 1E has the effects of the image pickup unit 1 and the image pickup units 1A to 1E.

The endoscope may be a flexible endoscope having a flexible insertion portion or a rigid endoscope having a rigid insertion portion. The endoscope may be used for medical or industrial purposes.

The present invention is not limited to the embodiments and the like described above, and various changes, combinations, and applications can be made within a scope without departing from the spirit of the present invention.

What is claimed is:

1. An image pickup unit comprising:
a first optical device including a lens and a spacer arranged around the lens, the spacer having a circular inner circumference, the spacer having a thickness in an optical axis direction of the lens that alternatively increases and decreases in a circumferential direction of the spacer to define a plurality of grooves and peaks comprising an adhesive surface;
an adhesive layer disposed on the adhesive surface of the spacer;
a second optical device adhered to the first optical device by the adhesive layer; and
an imager, comprising an image sensor, receiving light condensed by an optical system including the first optical device and the second optical device,
wherein the plurality of grooves and peaks of the adhesive surface are formed radially centered on an optical axis of the lens, the plurality of grooves and peaks extending continuously in the circumferential direction.

2. The image pickup unit according to claim 1, wherein each of the plurality of grooves and peaks have a V shape cross section.

3. The image pickup unit according to claim 1, wherein each of the plurality of grooves and peaks have a cross section configured by a curve.

4. The image pickup unit according to claim 1, wherein the first optical device is a hybrid lens device including a first transparent substrate, the lens made of a resin, and the spacer made of the resin.

5. The image pickup unit according to claim 1, wherein the spacer and the second optical device are in line contact.

6. An endoscope comprising:
an image pickup unit disposed at a distal end portion of an insertion portion, the image pickup unit comprising:
a first optical device including a lens, the spacer having a circular inner circumference, the spacer having a thickness in an optical axis direction of the lens that alternatively increases and decreases in a circumferential direction of the spacer to define a plurality of grooves and peaks comprising an adhesive surface;
an adhesive layer disposed on the adhesive surface of the spacer;
a second optical device adhered to the first optical device by the adhesive layer; and
an imager, comprising an image sensor, receiving light condensed by an optical system including the first optical device and the second optical device,
wherein the plurality of grooves and peaks of the adhesive surface are formed radially centered on an optical axis of the lens, the plurality of grooves and peaks extending continuously in the circumferential direction.

7. A method for manufacturing an image pickup unit, the method comprising:
fabricating a first wafer including a first optical device including a lens and a spacer arranged around the lens, the spacer having a circular inner circumference, the spacer having a thickness in an optical axis direction of the lens that alternatively increases and decreases in a circumferential direction of the spacer to define a plurality of grooves and peaks comprising an adhesive surface, and a second wafer including a second optical device;
disposing an adhesive layer made of an uncured adhesive on a flat plate;
transferring the adhesive to the adhesive surface by abutting the adhesive surface of the spacer of the first wafer against the adhesive layer on the flat plate and then separating the adhesive surface from the adhesive layer;
adhering the second wafer and the first wafer using the adhesive;
adhering an imager, comprising an image sensor, receiving light condensed by an optical system including the first optical device and the second optical device; and
cutting a stacked wafer including the first wafer, the second wafer, and the imager into singulated image pickup units each including the first optical device, the second optical device, and the imager such that the plurality of grooves and peaks of the adhesive surface are formed radially centered on an optical axis of the lens with the plurality of grooves and peaks extending continuously in the circumferential direction.

* * * * *